US012788366B2

(12) United States Patent
Falk et al.

(10) Patent No.: US 12,788,366 B2
(45) Date of Patent: Nov. 10, 2026

(54) FLEXIBLE SUBSTRATE ULTRASOUND TRANSDUCER SYSTEM AND METHOD FOR FETAL STRAIN AND HEART RATE MONITORING

(71) Applicant: GE Precision Healthcare LLC, Milwaukee, WI (US)

(72) Inventors: Steven M. Falk, Baltimore, MD (US); Sivaramanivas Ramaswamy, Bangalore (IN); Nagapriya Kavoori Sethumadhavan, Bangalore (IN); Vijith Venugopalan, Bangalore (IN); Kiran B. Kumar, Bangalore (IN); Karen P. Becker, Phoenix, MD (US); Dianne R. Kessler, Brentwood, TN (US)

(73) Assignee: GE Precision Healthcare LLC, Wauwatosa, WI (US)

(*) Notice: Subject to any disclaimer, the term of this patent is extended or adjusted under 35 U.S.C. 154(b) by 735 days.

(21) Appl. No.: 18/053,461

(22) Filed: Nov. 8, 2022

(65) Prior Publication Data

US 2024/0148363 A1 May 9, 2024

(51) Int. Cl.
*A61B 8/00* (2006.01)
*A61B 90/00* (2016.01)

(52) U.S. Cl.
CPC .......... *A61B 8/4488* (2013.01); *A61B 8/4209* (2013.01); *A61B 90/06* (2016.02); *A61B 2090/064* (2016.02); *A61B 2503/04* (2013.01)

(58) Field of Classification Search
CPC ..... A61B 8/4488; A61B 8/4209; A61B 90/06; A61B 2090/064; A61B 2503/04;
(Continued)

(56) References Cited

U.S. PATENT DOCUMENTS

| | | | |
|---|---|---|---|
| 9,440,258 | B2 | 9/2016 | Klee et al. |
| 9,820,718 | B2 | 11/2017 | Flomerfelt et al. |

(Continued)

FOREIGN PATENT DOCUMENTS

| | | | |
|---|---|---|---|
| CN | 101894855 | A | 11/2010 |
| CN | 112220491 | A | 1/2021 |

(Continued)

OTHER PUBLICATIONS

Hamelmann et al., Fetal Heart Rate Monitoring Implemented by Dynamic Adaptation of Transmission Power of a Flexible Ultrasound Transducer Array, Sensors, 2019, 19, 1195, 20 pages.

(Continued)

*Primary Examiner* — Serkan Akar

(57) ABSTRACT

An ultrasound system includes a transducer array including a flexible substrate, ultrasound transducer elements disposed on the flexible substrate and configured to transmit and acquire ultrasound signals that propagate in a body of a patient, and strain sensors coupled to or integrated into the flexible substrate and configured to measure a strain in the flexible substrate generated by flexing the flexible substrate. The ultrasound system also includes a processor coupled to the ultrasound transducer elements and the strain sensors, wherein the processor is configured to process the signals acquired by the ultrasound transducer elements based at least in part on the strain measured by the strain sensors.

7 Claims, 11 Drawing Sheets

(58) Field of Classification Search
CPC ....... A61B 8/02; A61B 8/0866; A61B 8/0883; A61B 8/4494; A61B 8/4483; A61B 8/4227; A61B 8/4281; G01S 15/8936
See application file for complete search history.

(56) References Cited

U.S. PATENT DOCUMENTS

| | | | | |
|---|---|---|---|---|
| 11,064,924 | B2 | 7/2021 | Woltjer et al. | |
| 11,213,275 | B2 | 1/2022 | Hakkens et al. | |
| 2007/0078345 | A1 * | 4/2007 | Mo .......................... | A61B 8/12 600/459 |
| 2013/0331704 | A1 | 12/2013 | Salzman | |
| 2018/0168544 | A1 | 6/2018 | Davidsen | |
| 2021/0059634 | A1 | 3/2021 | Hamelmann | |

FOREIGN PATENT DOCUMENTS

| | | | |
|---|---|---|---|
| EP | 1750587 | A4 | 8/2009 |
| EP | 3708263 | A1 | 9/2020 |
| EP | 3840830 | A1 | 6/2021 |
| EP | 3881770 | A1 | 9/2021 |
| WO | 2021099618 | A1 | 5/2021 |

OTHER PUBLICATIONS

EP application 23205139.1 filed Oct. 23, 2023—Search Report issued Mar. 13, 2024; 7 pages.

* cited by examiner

FLEXIBLE SUBSTRATE ULTRASOUND TRANSDUCER SYSTEM AND METHOD FOR FETAL STRAIN AND HEART RATE MONITORING

BACKGROUND

The subject matter disclosed herein relates to medical imaging and, in particular, a flexible ultrasound imaging device for monitoring the health of a fetus (or multiple-fetuses, ante-partum), an infant (post-partum), a mother, and/or other health metrics, which may be worn or otherwise connected to a patient such as a mother or infant.

An ultrasound device may be used for imaging targets such as organs and soft tissues in a human body, as well non-human targets. For example, an ultrasound device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc. Such devices are frequently used ante-partum, secured to a mother and used to measure health-related metrics of the mother and/or the fetus (or fetuses). Further, ultrasound imaging devices are used to acquire health data for infants, post-partum.

Ultrasound devices may use real-time, non-invasive high frequency sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target.

Ultrasound imaging devices typically include sensors that are hand-held or may be strapped or otherwise secured to the body of a patient, generally an adult, e.g., to the abdomen of a mother during labor to measure maternal and/or fetal heartrates. A common issue encountered with such devices is that movement of the fetus generally requires frequent repositioning the sensor on the mother's body to acquire a desired signal.

Moreover, using these sensors to monitor infants may not be suitable because the relatively small and delicate bodies of newborns may not easily permit such conventional sensors to be worn. Thus, infrequent and sometimes inconvenient monitoring techniques are used. For example, the infants may be placed into a machine that produces the ultrasound images. However, this presents several drawbacks. First, the infant typically cannot stay within the ultrasound machine for long, and thus the ultrasonic monitoring is infrequent not continuous. Moreover, the machines may not be readily available, and thus there may be a time delay between when ultrasound measurements are desired and when they become available. Further, moving machines between locations (e.g., hospital rooms, beds, etc.) may present difficulties. Additionally, some types of imaging, which may be used, such as X-ray, may emit radiation that is harmful to the patient, but may permit continuous monitoring of the patient, e.g., for guiding medical procedures.

SUMMARY

Certain implementations commensurate in scope with the originally claimed subject matter are summarized below. These implementations are not intended to limit the scope of the claimed subject matter, but rather these implementations are intended only to provide a brief summary of possible forms of the subject matter. Indeed, the subject matter may encompass a variety of forms that may be similar to or different from the implementations set forth below.

An ultrasound system is disclosed. The ultrasound system includes a transducer array including a flexible substrate, ultrasound transducer elements disposed on the flexible substrate and configured to transmit and acquire ultrasound signals that propagate in a body of a patient, and strain sensors coupled to or integrated into the flexible substrate and configured to measure a strain in the flexible substrate generated by flexing the flexible substrate. The ultrasound system also includes a processor coupled to the ultrasound transducer elements and the strain sensors. The processor is configured to process the signals acquired by the ultrasound transducer elements based at least in part on the strain measured by the strain sensors.

In some implementations, the strain sensors are configured to measure a stretch, a stretch direction, or both, and the processor is configured to calculate positions of the ultrasound transducer elements relative to one another based at least in part on the strain, the stretch, the stretch direction, or a combination thereof.

In some implementations, the processor is configured to modify transmission and reception time-delay parameters based at least in part on the calculated positions.

In some implementations, the processor is configured to construct an image based on the ultrasound signals, and the image represents one or more of lungs, body fluid, cardiac imaging, hear rate, respiration rate, gastrointestinal organs, or brain development.

In some implementations, the strain sensors are disposed on the flexible substrate.

In some implementations, the strain sensors are interspersed with the ultrasound transducer elements on the flexible substrate.

In some implementations, the transducer array is configured to be coupled to a clothing garment that is worn by the patient, the patient being an infant.

In some implementations, the transducer array is coupled to a wearable band configured to be secured to an abdomen of a patient, the patient being a pregnant mother, and the transducer array is configured to detect a heart rate of one or more fetuses in the pregnant mother, a heart rate of the mother, uterine activity within the pregnant mother, fetal movement, fetal position and descent, or a combination thereof.

In some implementations, the transducer array is configured to continuously transmit signals to the processor, and the processor is configured to continuously interpret the signals to monitor a health of the patient.

A method is disclosed, including positioning a transducer array on a patient. The transducer array includes a flexible substrate, a plurality of ultrasound transducer elements disposed on the flexible substrate, and a plurality of strain sensors coupled to the flexible substrate and configured to generate signals representing a strain in the flexible substrate generated by flexing the flexible substrate. The method includes energizing the transducer array such that at least some of the plurality of ultrasound transducer elements emit and receive ultrasound signals and the strain sensors measure the strain, receiving, using a processor, data representing the ultrasound signals received by at least some of the ultrasound transducer elements and data representing the strain measured by at least some of the strain sensors, determining, using the processor, a beamforming parameter based at least in part on the strain, and generating an image, a health statistic, or both representing at least a part of the patient based at least in part on the ultrasound signals and the beamforming parameter.

In some implementations, the method includes guiding a medical procedure on the patient using the image.

In some implementations, guiding the medical procedure includes providing guidance for inserting a tube into the patient, and generating the image, health statistic, or both includes continuously imaging for a duration of time to ensure that the tube remains in place.

In some implementations, determining the signal processing parameter includes determining relative positions of at least some of the ultrasound transducer elements based at least in part on the strain, and adjusting the beamforming parameter for respective transducer elements based at least in part on the relative positions.

In some implementations, the strain sensors are configured to measure a stretch, stretch direction, or both, and determining the relative positions is based at least in part on the stretch, the stretch direction, or both.

In some implementations, the method includes applying a predetermined voltage to the strain sensors so as to calibrate a position of the ultrasound transducer elements relative to one another.

In some implementations, imaging includes generating an image representing one or more of lungs, body fluid status, cardiac status, heart rate, respiration rate, gastrointestinal status, brain development.

In some implementations, the method includes coupling the transducer array to a clothing garment. In such implementations, positioning the transducer array on the patient includes putting the clothing garment on the patient, the patient being an infant.

In some implementations, the method includes coupling the transducer array to a flexible belt. In such implementations, positioning the transducer array on the patent includes putting the flexible belt around an abdomen of the patent, the patient being a pregnant woman.

A system for ultrasound imaging is disclosed. The system includes a garment configured to fit onto a patient, a transducer array secured to the garment and including a flexible substrate, ultrasound transducer elements disposed on the flexible substrate and configured to transmit and acquire ultrasound signals that propagate in a body of a patient, and strain sensors coupled to the flexible substrate and configured to measure a strain in the flexible substrate generated by flexing the flexible substrate to conform to a body of the patient, and a processor configured to communicate with the ultrasound transducer elements and the strain sensors. The processor is configured to determine a beamforming parameter for the ultrasound transducer elements based at least in part on the strain measured by the strain sensors, and the processor is configured to generate an image of a part of the patient based at least in part on the beamforming parameter and the ultrasound signals acquired by the ultrasound transducer elements.

In some implementations, the strain sensors include piezo-polymer material, and the ultrasound transducer elements comprise ultrasonic Doppler sensors, ultrasonic imaging sensors, or both.

In some implementations, the strain sensors are configured to measure a stretch and stretch direction, and the processor is configured to determine the beamforming parameter based at least in part on the stretch and stretch direction.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

Detailed Description

Figure 1:
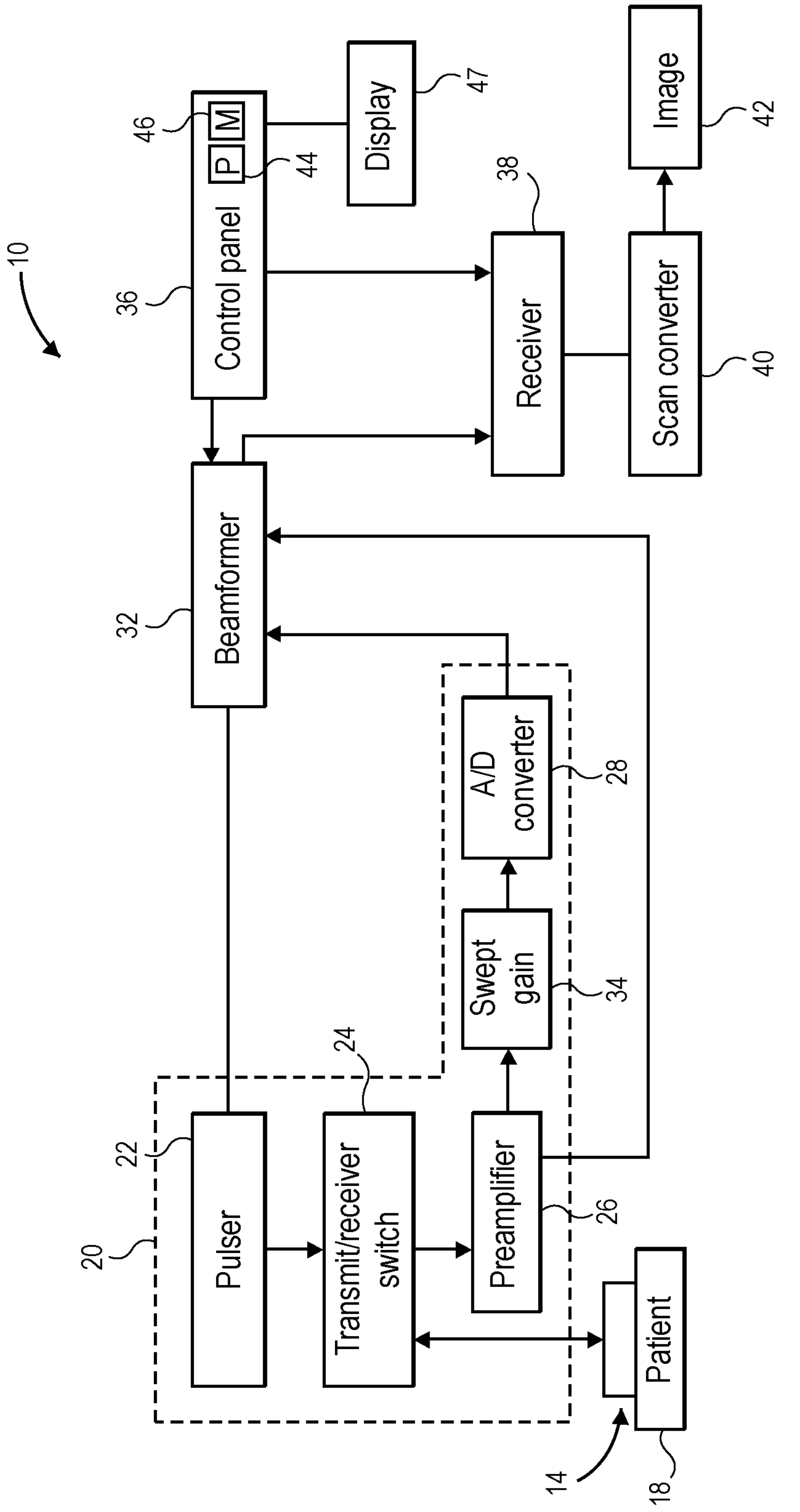
FIG. 1 depicts a simplified schematic view of components of an ultrasound sensor system, according to an example.

| Element | Reference Number |
|---|---|
| Ultrasound sensor system | 10 |
| Transducer array | 14 |
| Patient | 18 |
| Application specific integrated circuit (ASIC) | 20 |
| Pulser | 22 |
| Switch | 24 |
| Preamplifier | 26 |
| D Converter | 28 |
| Beam-former | 32 |
| Gain | 34 |
| Control Panel | 36 |
| Receiver | 38 |
| Scan Converter | 40 |
| Images | 42 |
| Processing component | 44 |
| Memory | 46 |
| Display | 47 |
| Transducer array | 200, 200-1, 200-2, 200-3 |
| Flexible substrate | 202 |
| Strain Sensors | 204 |
| Ultrasound transducer elements | 206 |
| Charge amplfier | 210 |
| Voltage array | 212 |
| Dsiplacement | 214 |
| Main body | 300 |
| Surface | 300A |
| Surface | 300B |
| Electrode | 301 |
| Electrode | 302 |
| Focal point | 400 |
| Constant phase front | 402 |
| Time-delay bar | 404 |
| Ultrasound signal | 406 |
| Wearable clothing garmet | 800 |
| Processor | 802 |
| Conductive cables | 804 |

-continued

| Detailed Description | |
|---|---|
| Element | Reference Number |
| Flexible belt | 850 |
| Monitor | 852 |
| Computing system | 1000 |
| Individual computing system | 1001a, 1001b, 1001c, 1001d |
| Analysis module(s) | 1002 |
| Processor(s) | 1004 |
| Storage media | 1006 |
| Network interface | 1007 |
| Signal adjustment module | 1008 |
| Data network | 1009 |

One or more specific implementations will be described below. In an effort to provide a concise description of these implementations, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various implementations of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed implementations.

As used herein, the term "image" broadly refers to both viewable images and data representing a viewable image. However, many implementations may generate (or are configured to generate) at least one viewable image. In addition, as used herein, the phrase "image" is used to refer to ultrasound images such as, for example, B-mode (2D mode), M-mode, three-dimensional (3D) mode, CF-mode, PW Doppler, CW Doppler, B-flow, Furthermore, the term processor or processing unit, as used herein, refers to any type of processing unit that can carry out the required calculations needed for the various implementations, such as single or multi-core: CPU, Accelerated Processing Unit (APU), Graphics Board, DSP, FPGA, ASIC or a combination thereof.

The present disclosure addresses the challenges noted above and/or others by provision of a flexible ultrasound transducer array that may be used to continuously monitor various health metrics and/or construct images of a patient, e.g., an infant, a fetus, a mother, etc. In particular, the sensor may be coupled to clothing that may be worn. Further, the sensor system is configured to account for flexing using strain sensors, which may permit an inference as to the relative location of ultrasound transducer elements that are provided in the flexible ultrasound sensor. The relative location can then be used to modify delay laws, beamforming, and/or other parameters, in order to permit aligning signals from the different ultrasound transducer elements and thereby provide an accurate measurement/image. These and other aspects of the present invention are discussed in greater detail below, and the foregoing paragraph is not intended to limit the scope of the disclosure.

With the preceding in mind, turning to the specifically illustrated implementations, FIG. 1 depicts a high-level view of components of an ultrasound system 10, according to an example. The illustrated ultrasound system 10 includes a transducer array 14 having ultrasound transducer elements (e.g., piezoelectric crystals) suitable for contact with a subject or patient 18 during an imaging procedure, and strain sensors. The transducer elements of the transducer array 14 may be configured as two-way transducers capable of transmitting ultrasound waves into and receiving such energy from the subject or patient 18. In such an implementation, in the transmission mode, the ultrasound transducer elements convert electrical energy into ultrasound signals and transmit it into the patient 18. In reception mode, the ultrasound transducer array elements convert reflected ultrasound signals that have propagated in the patient 18 (backscattered waves) into electrical signals (or ultrasound data). As will be described in greater detail below, the transducer elements and strain sensors may be positioned in, on, or otherwise be coupled to, a flexible substrate.

Each transducer element is associated with respective transducer circuitry, which may be provided as one or more application specific integrated circuits (ASICs) 20. The ASIC 20 may be external to the transducer array 14 and in communication therewith via a wired or wireless link. In some implementations, the ASIC 20 may be present in (e.g., in the same housing as) the transducer array 14. In some implementations, individual transducer elements in the transducer array 14 may be electrically connected to a respective pulser 22, transmit/receive switch 24, preamplifier 26, swept gain 34, and/or analog to digital (A/D) converter 28 provided as part of or on an ASIC 20. In other implementations, this arrangement may be simplified or otherwise changed. For example, components shown in the ASIC 20 may be provided upstream or downstream of the depicted arrangement; however, the basic functionality depicted may be provided for each transducer element. In the depicted example, the referenced circuit functions are conceptualized as being implemented on a single ASIC 20 (denoted by dashed line); however, some or all of these functions may be provided on the same or different integrated circuits. The ASIC 20 may be used to control the switching of the transducer elements. The ASIC 20 may also be used to group the transducer elements into one or more sub-apertures (e.g., in response to control signals from the control panel 36).

Also depicted in FIG. 1, a variety of other imaging components are provided for image formation with the ultrasound system 10. Specifically, the depicted example of an ultrasound system 10 also includes a beam-former 32, a control panel 36, a receiver 38, and a scan converter 40 that cooperate with the transducer circuitry to produce an image or series of images 42 that may be stored and/or displayed to an operator or otherwise processed as discussed herein. The transducer array 14 may communicate the ultrasound data to the beam-former 32 via a wired connection or wireless connection (e.g., via a wireless communication unit that is part of the transducer array that communicates over a wi-fi network, utilizing BLUETOOTH® technique, or some other manner). A processing component 44 (e.g., a microprocessor) and a memory 46 of the system 10, such as may be present in control panel 36, may be used to execute stored routines for processing the acquired ultrasound signals to generate meaningful images and/or motion frames, which may be displayed on a display 47 of the ultrasound system 10. The processing component 44 may also be configured to convert strain in the flexible substrate on which the transducer array 14 is positioned into displacement data, and calculate various signal acquisition parameters based thereon, as will be described in greater detail below.

Ultrasound information may be processed by other or different mode-related modules (e.g., B-mode, Color Doppler, power Doppler, M-mode, spectral Doppler anatomical M-mode, strain, strain rate, and the like) to form 2D or 3D data sets of image frames and the like. For example, one or more modules may generate B-mode, color Doppler, power Doppler, M-mode, anatomical M-mode, strain, strain rate, spectral Doppler image frames and combinations thereof, and the like. The image frames are stored and timing information indicating a time at which the image frame was acquired in memory may be recorded with each image frame. The modules may include, for example, a scan conversion module to perform scan conversion operations to convert the image frames from Polar to Cartesian coordinates. A video processor module may be provided that reads the image frames from a memory and displays the image frames in real time while a procedure is being carried out on a patient. A video processor module may store the image frames in an image memory, from which the images are read and displayed. The ultrasound system 10 shown may comprise a console system, or a portable system, such as a hand-held or laptop-type system.

The ultrasound system 10 may be operable to continuously acquire ultrasound scan data at a frame rate that is suitable for the imaging situation in which it is used. Frame rates may range from 20-120, but may be lower or higher. The acquired ultrasound scan data may be displayed on the display 47 at a display rate that can be the same as the frame rate, or slower or faster. An image buffer may be included for storing processed frames of acquired ultrasound scan data that are not scheduled to be displayed immediately. In some examples, the image buffer is of sufficient capacity to store frames of potentially several minutes of ultrasound scans. The frames of ultrasound scan data are stored in a manner to facilitate retrieval thereof according to its order or time of acquisition. The image buffer may be embodied as any known data storage medium.

The display 47 may be any device capable of communicating visual information to a user. For example, the display 47 may include a liquid crystal display, a light emitting diode display, and/or any suitable display or displays. The display 47 can be operable to present ultrasound images and/or any suitable information.

Components of the ultrasound system 10 may be implemented in software, hardware, firmware, and/or the like. The various components of the ultrasound system 10 may be communicatively linked. Components of the ultrasound system 10 may be implemented separately and/or integrated in various forms.

Figure 2:
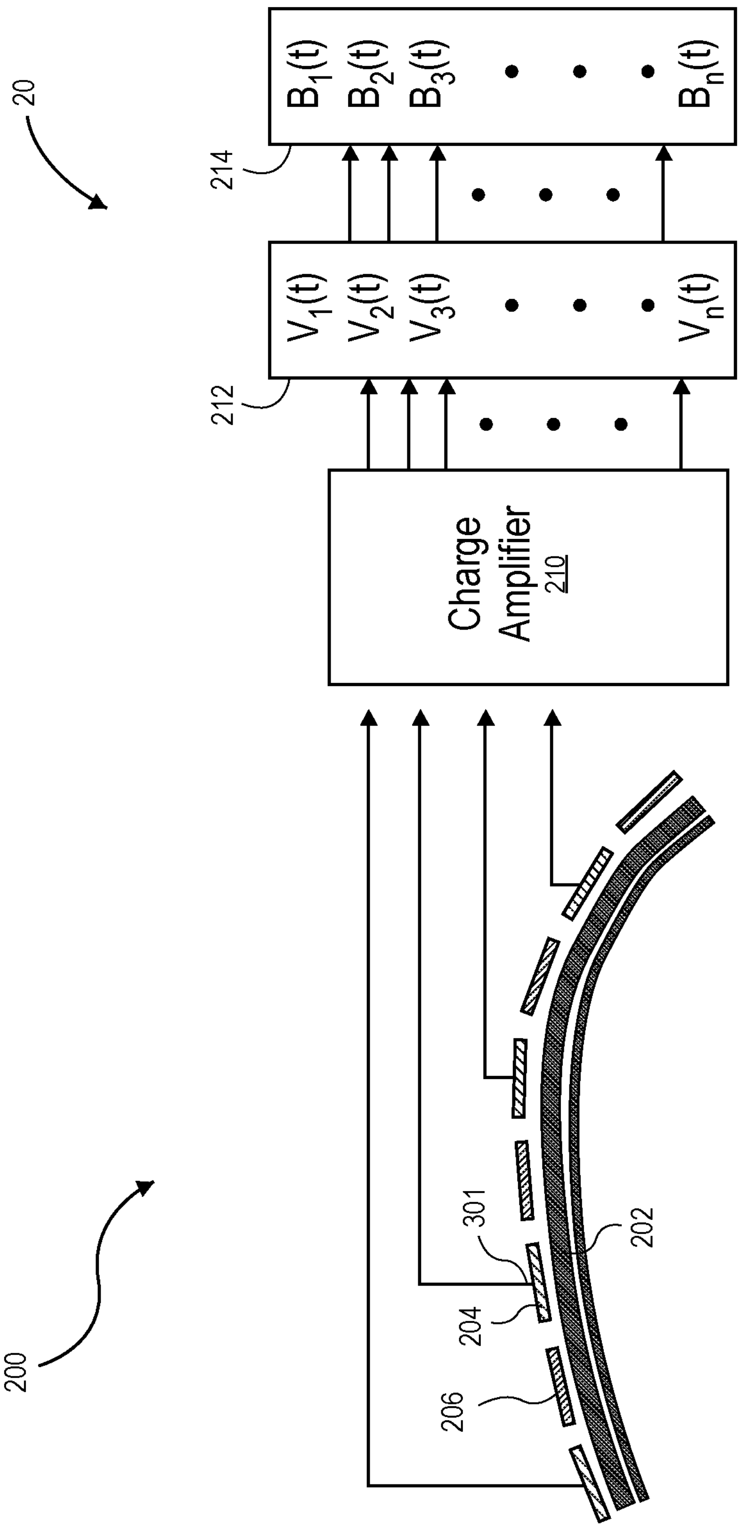
FIG. 2 illustrates a simplified schematic view of at least a portion of a transducer array of the ultrasound system, according to an example.

FIG. 2 illustrates a schematic view of at least a portion of an ultrasound transducer array 200, according to an example. The ultrasound transducer array 200 may, for example, be part of the ultrasound system 10, e.g., providing the transducer array 14 and one or more portions of the ASIC 20 of FIG. 1. As shown, the transducer array 200 may include a substrate 202, one or more strain sensors 204, and an array of ultrasound transducer elements (e.g., piezoelectric crystals) 206. In some examples, many strain sensors 204 may be provided, e.g., equal to or greater than the number of ultrasound transducer elements 206. The strain sensors 204 may be relatively small (compared to the substrate 202) patches that are interspersed among the ultrasound transducer elements 206. In some implementations, the strain sensors 204 may be uniformly distributed, e.g., interleaved between each adjacent pair of ultrasound transducer elements 206. In other implementations, the strain sensors 204 may be non-uniformly distributed, e.g., between some pairs of adjacent ultrasound transducer elements 206, but not between others, and/or two or more strain sensors 204 may be disposed between a single pair of ultrasound transducer elements 206. The strain sensors 204 may be flexible, as will be described in greater detail below, and may be configured to measure strain applied thereto and/or apply a strain to the substrate 202.

As shown, the substrate 202 may be a relatively flexible material, e.g., able to elastically deflect over a large distance (relative to its size) without yielding. A variety of different materials may be suitable for such a substrate including ferro-electric polymers from PVDF family of materials. Further, as can also be seen FIG. 2, the ultrasound transducer elements 206 and the strain sensors 204 may be relatively small in size and separated apart, which may provide articulation to complement, rather than impair, the flexibility of the substrate 202, permitting the substrate 202 to flex. The flexibility of the substrate 202 may result in the transducer array 200 being readily conformable to the contours of a patient's body, e.g., an infant's body, a mother's body, etc., and may thus be coupled to clothing, bed linens, etc., as will be described in greater detail below.

The ultrasound transducer elements 206 may be positioned on, embedded in, or otherwise connected to the flexible substrate 202. Further, the ultrasound transducer elements 206 may include one or more ultrasonic Doppler sensors, ultrasonic imaging sensors, or a combination thereof. The ultrasound transducer elements 206 may be configured to convert electrical power to ultrasonic Doppler signals, ultrasonic images, or any other suitable signal type, and thereby emit an ultrasonic signal in a selected direction. The transducer elements 206 may also be configured to convert received ultrasonic Doppler signals to electrical signals. In certain examples, the transducer elements 206 may be made of lead zirconate titanate (PZT). The number of transducer elements 206 forming the transducer array 200 vary from 10 to 100 or more transducer elements 206. During operation, the transducer elements 206 function to acquire data for locating multiple fetuses within a uterus and/or measuring heart rates (e.g., maternal heart rate and fetal heart rate of each fetus).

The transducer elements 206 may form or include a steerable array of piezoelectric crystals, which may be steerable to control a trajectory of the signals, such that echoes (reflections, backscatter signals) therefrom represent one or more health measurements of a patient, e.g., body fluid status, cardiac status, heart rate, respiration rate, gastrointestinal status, brain development. Further, the acquired signals may be employed to generate images, such as images of the lungs, brain, heart, gastrointestinal system, etc. In other examples, one or more of the transducer elements 206 may be configured to transmit and not to receive, while another may be configured to receive and not transmit. Various combinations of ultrasound transducer elements 206 may be employed.

Different subsets (e.g., two or more transducer elements 206, but less than the total number of transducer elements 206) of the transducer elements 206 may be triggered or fired sequentially (i.e., to transmit ultrasound waves). Thus, one subset of transducer elements 206 may be fired or triggered, then a different subset of transducer elements 206 may be fired or triggered, and the firing sequence continues until each of the transducer elements 206 have been fired or triggered. The firing sequence may thus refer to the order in which the different transducer elements 206 are fired and/or which transducer elements 206 are fired, which may impact the focus of the transducer array 200. In certain examples, the data is acquired utilizing sub-aperture FMC. In certain examples, the data is acquired in low resolution B-mode to localize and track fetal movement (e.g., where individual rows of transducer elements 206 are sequentially fired with each subsequent fired row being adjacent to the previously fired row). In some examples, multi-plane low resolution B-mode images are reconstructed, e.g., to localize fetuses when the ultrasound transducer array 200 is applied to a mother. In some examples, the transducer elements 206 may be sequentially fired or triggered individually (as opposed to with a subset). The different subsets may have the same number of transducer elements 206 or vary in the number of transducer elements 206 making up the subset.

The transducer elements 206 of the array receive the ultrasound energy returned from the patient. For example, if six of the transducer elements 206 form a subset of transducer elements 206, and another transducer element 206, which is not part of the subset, transmits ultrasound waves, then both the six of the subset, the one that emitted, and any others of the transducer elements 206 may receive the ultrasound energy returned from the patient. This utilization of the transducer elements 206 ensures sufficient depth of field for Doppler measurements to enable measurement of the heart rates (e.g., fetal and maternal). As described in greater detail below, the acquisition of scan data from the sequential firing of the transducer elements enables targeting, e.g., the localization of the different fetuses within the uterus. In addition, as described in greater detail below, adjusting where to focus the transducer elements 206 and/or changing the firing sequence (e.g., timing) of the transducer elements 206 may permit the transducer array 200 to be kept in place (i.e., not readjusting the transducer's position) when one or more fetuses move or shifting the target of the transducer elements 206 is otherwise desired.

The strain sensors 204 may be coupled to the flexible substrate 202 and/or integrated therein. In some examples, the flexible substrate 202 may be at least partially constructed of a material that reacts proportionally to applied strain. In such case, the strain sensors 204 are considered herein to be "integrated" into the flexible substrate 202. In various examples, the strain sensors 204 may be at least partially embedded in, positioned on, adhered to, or otherwise connected directly to the substrate 202, such that the strain sensors 204 may be configured to measure a strain and thus permit inference of a deflection of the substrate 202. In a specific example, the sensors 204 may be made from a piezo-polymeric material. Briefly, piezo-polymer materials generate a voltage proportional to the thinning and thickening of the layer of material as they are bent. Thus, as a material is bent, the area of the material in which a radius of curvature develops may generate a voltage as its thickness changes. This can be measured to permit a strain to be inferred. The piezo-polymer material can thus provide "stretchable" strain sensors. Moreover, a strain direction can be determined, e.g., based on the polarity of the voltage that is generated. The strain sensors 204 may also be capable of deforming in response to an applied voltage, as will be described in greater detail below, and thus may serve as drivers to deform the flexible substrate 202, in at least some examples.

Figure 3:
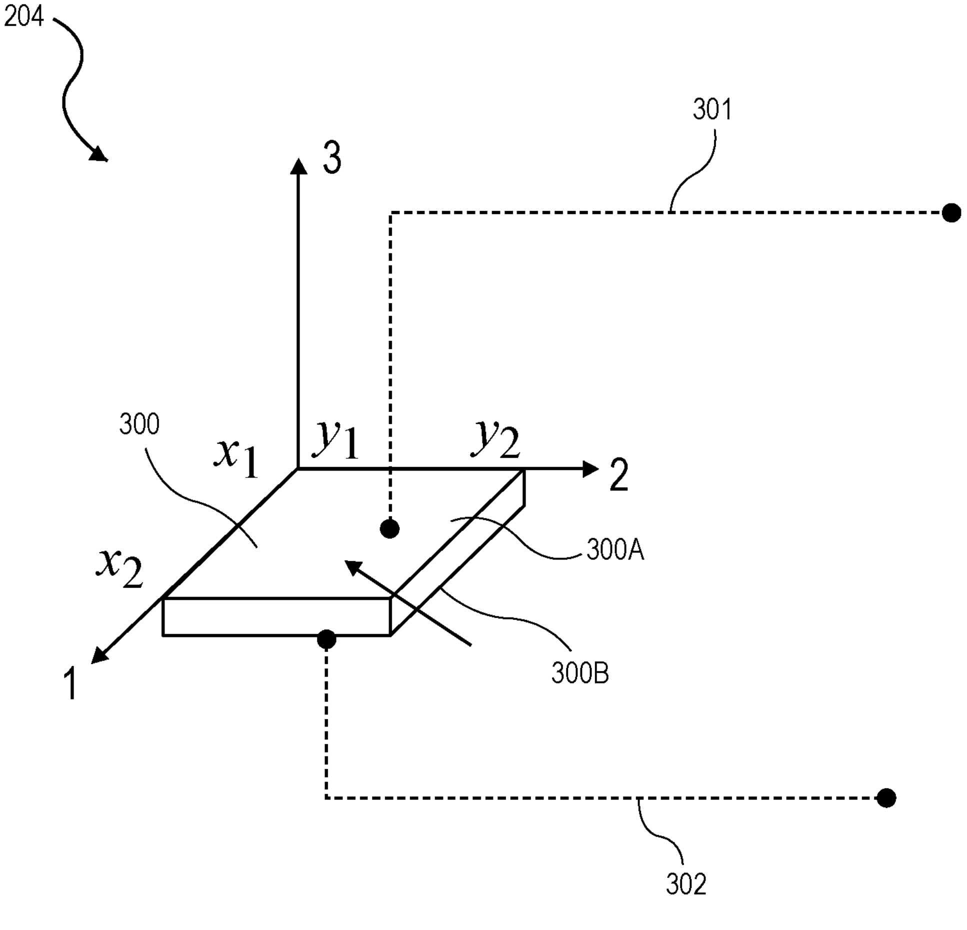
FIG. 3 illustrates a simplified perspective view of a strain sensor, according to an example.

FIG. 3 illustrates a simplified perspective view of a strain sensor 204, according to an example. As shown, the strain sensor 204 may have a generally planar, main body 300, for example, providing the "patch" mentioned above. For example, this view provides a coordinate system to assist in describing the main body 300. The coordinate system includes axis-1, axis-2, and axis-3. Axis-1 (x-axis) and axis-2 (y-axis) may generally define the horizontal plan, with the main body 300 being generally within the x-y plane when not bent. Axis-3 (z-axis) may define the vertical axis, normal to the main body 300, with the main body 300 having a thickness in the axis-3. Changes in the thickness may result in a voltage differential developing across opposing surfaces 300A, 300B of the main body 300 in the axis-3 direction.

The main body 300 may be made at least partially of a piezo-polymer material. Electrodes 301, 302 may be connected to opposing surfaces 300A, 300B of the main body 300 and may be configured to detect a voltage differential therebetween. When a strain is experienced in the main body 300, e.g., tending to bend the main body 300 out of the x-y plane of the axis-1 and axis-2, the thickness (along axis 3) may reduce as a consequence, thereby producing a transient, but measurable voltage. Such voltage may be proportional to the strain, and from the strain, the deflection of the main body 300 can be determined. Further, the polarity of the voltage can indicate in which direction the main body 300 is strained. With both deflection amount and direction determined, a geometry of the main body 300 can be determined.

Thus, referring again to FIG. 2, with potentially many strain sensors 204 attached to the flexible substrate 202, a shape of the flexible substrate 202 under a bending load can be determined. Once the shape of the flexible substrate 202 is determined, the relative positions of the ultrasound transducer elements 206 may likewise be inferred.

In more specific terms, deformation of the piezo-polymeric main body 300 may result in a strain field. The strain field may be the derivative of a displacement field (referring to the change in shape of the main body 300). Considering the effect of strain along the axis-1 direction, the equation relating strain (6) and voltage (V) generated by the main body 300 is:

$$\varepsilon = \frac{VC}{S}$$

In this equation, C refers to capacitance and S refers to a sensitivity factor of the piezo-polymeric material, which may be different for different materials/geometries. The strain ε measured by the sensor 204 may be the average of the strain field over the area of the main body 300. This average can be found from the double integral of the strain field over the length and width of the area of the main body, as follows:

$$\varepsilon = \frac{1}{(x_2 - x_1)(y_2 - y_1)} \int_{y_1}^{y_2} (u(x_2 - y) - u(x_1 - y))dy$$

In this equation, for a two-dimensional main body 300, a specific case where variation along axis-2 (y) of FIG. 3 is held constant is shown. Thus, measurement of voltage across each sensor 204 may provide for an estimation of the displacement (stretch) of each of the sensors 204, and thus the flexible substrate 202, and then the relative position of the ultrasound transducer elements 206 positioned thereon.

Figure 4:
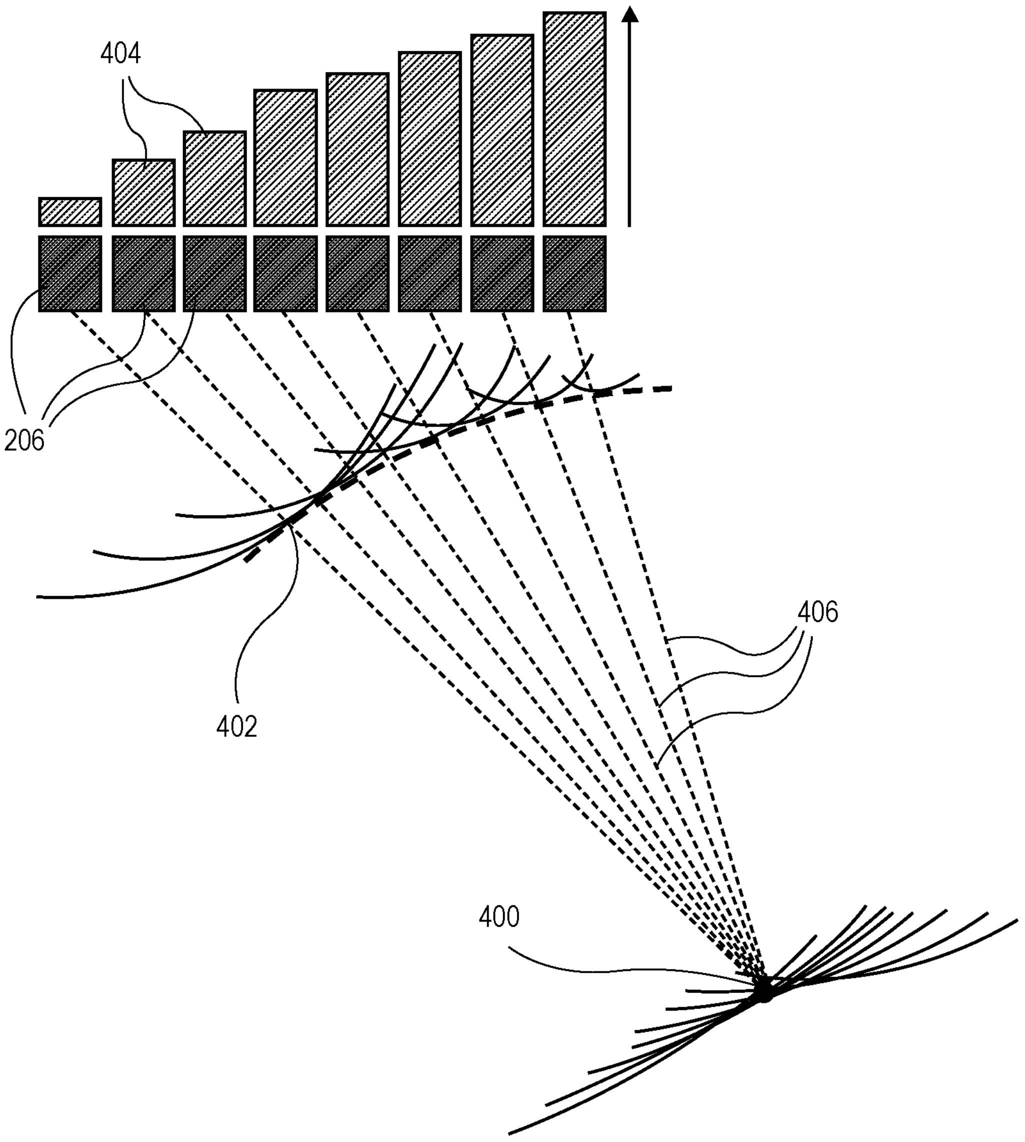
FIG. 4 illustrates a schematic view of the array of ultrasound transducer elements, according to an example.

FIG. 4 illustrates a schematic view of the array of ultrasound transducer elements 206, according to an example. In this view, it is seen that the individual ultrasound transducer elements 206 may be aimed at a target represented by the focal point 400. A constant phase front 402 may thus exist, which is intersected by each signal (represented as a dashed line) 406 that is emitted and/or received by the individual ultrasound transducer elements 206. For example, in some cases, the signals 406 may be considered to propagate through the same medium, and thus may travel at the same speed, but in other cases, may travel at different speeds. The constant phase front 402 may represent a location that is the same time from the focal point 400 along each of the signals 406, such that a signal reflected from the focal point 400 along each of the signals 406 reaches the constant phase front 402 simultaneously. Because the ultrasound transducer elements 206 are not all the same distance from the constant phase front 402, a time-delay law—a parameter (e.g., time-delay parameter) represented as bars 404 stemming from each transducer element 206 associated therewith, with a longer bar 404 representing a proportionally longer time-delay law—is applied that is generally inversely proportional to the distance between the constant phase front 402 and the individual ultrasound transducer elements 206. This represents an inverse of the time required for the signal to travel between the constant phase front 402 and the individual transducer element 206. For example, in this view, the signal 406 reaches the right-most transducer element 206 first, followed by its neighbor to the left, and in sequence until reaching the left-most transducer element 206. Thus, to align the signals, the delay is longer for the transducer on the right than for that on the left.

The time-delay law (e.g., parameter), which is useful in accurately imaging objects at the focal point 400, may thus be at least partially dependent upon the relative positioning of the individual ultrasound transducer elements 206. Referring again to FIG. 2, with a flexible substrate 202, the relative positioning of the transducer elements 206 may not be static, but dynamic, e.g., depending on the bending of the substrate 202, which in turn depends on the movement and contours of the patient. As described above, the strain sensors 204 may provide information from which the geometry of the flexible substrate 202 may be determined. From this information, the relative positioning of the ultrasound transducer elements 206 on the flexible substrate 202 may be calculated. As a consequence, the time delays laws may be calculated, e.g., continuously, permitting accurate imaging of (or other data collection representing) the patient, notwithstanding movement and bending of the substrate 202, etc.

Still referring to FIG. 2, for example, as mentioned above, the strain sensors 204 may have electrodes 301 connected thereto (one shown for each in this view. Another electrode 302, shown in FIG. 3 but not visible in FIG. 2, may be connected to a common ground/neutral, for example). The electrode 301 may be connected to a charge amplifier 210. The charge amplifier 210 may be configured to amplify the relatively weak signal from the strain sensors 204 to a voltage that is convenient for operations using conventional circuitry. The output of the charge amplifier 210 may be an array of voltages 212 (e.g., voltage-time functions), e.g., one for each of the individual strain sensors 204. From the voltage array 212, displacement functions (e.g., displacement as a function of time) 214 may be calculated. A baseline position of the individual transducer elements 206 may be a priori established, and thus the displacement calculations (including distance and direction) may permit a time-based tracking of the positions of the individual transducer elements 206 relatively to one another. These positions may be used to adjust time-delay laws, e.g., on the fly or based on timestamps of transducer element 206 data acquisition, thereby permitting calibration of the transducer element 206 data.

Figure 5:
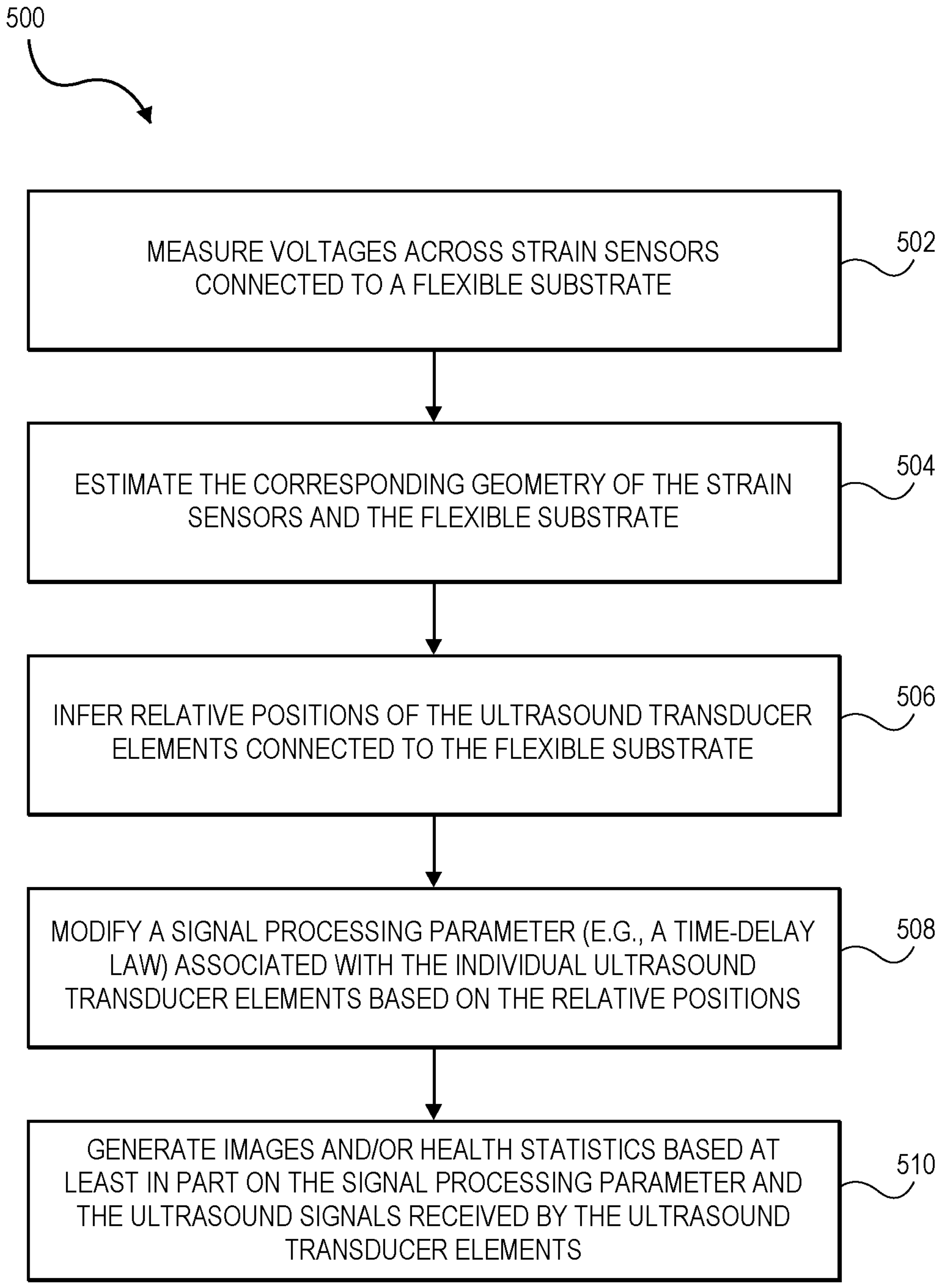
FIG. 5 illustrates a flowchart of a method for health monitoring using an ultrasound sensor system, according to an example.

FIG. 5 illustrates a flowchart of a method 500 for ultrasound signal acquisition, according to an example. The method 500 may proceed by operation of the ultrasound sensor system 10, but certain implementations may use other devices. Moreover, the method 500 may proceed by executing the steps in the order presented below, or in any other order, without departing from the scope of the present disclosure. In some examples, the steps presented herein may be combined, conducted in parallel, and/or individual steps may be partitioned into two or more steps, without departing from the scope of the present disclosure.

The present example may begin by measuring voltages across each of the strain sensors 204, as at 502. The method 500 may then include estimating the corresponding geometry of the strain sensors 204 and the flexible substrate 202 based at least in part on the voltages, as at 504. Such estimating may be conducted using a processor, such as a processor in the ASIC 20 (FIG. 1), or any other component of the ultrasound sensor system 10 of FIG. 1. The method 500 may then include inferring relative positions (e.g., based on displacement) of the ultrasound transducer elements 206 relative to one another, based at least in part on the geometry of the strain sensors 204 and/or the flexible substrate 202, as at 506. Again, this may be performed using a processor in the ultrasound sensor system 10 of FIG. 1 or an external processor.

The method 500 may then include modifying a signal processing parameter based at least in part on the relative positions, as at 508. This may be conducted using a processor. For example, the parameter may be configured to adjust a transmission and/or receiver time-delay law associated with the individual ultrasound transducer elements 206. For example, the ultrasound transducer elements 206 that are calculated to be closer to a target (e.g., focal point 400 of FIG. 4) of the transducer array 200 may have a longer time-delay law applied thereto than the time-delay law applied to ultrasound transducer elements 206 that are closer to the target. As such, the signals 406 received by the ultrasound transducer elements 206 may be aligned so as to correct for the transducer elements 206 not being on a constant phase front 402. Once the signals 406 are aligned, the method 500 may proceed to generating images or other health statistics based thereon, as at 510, e.g., using one or more processors of the ultrasound sensor system 10 of FIG. 1. Accordingly, it may be appreciated that the one or more processors generate the image(s) based in part on the time-delay law that was calculated.

Figure 6:
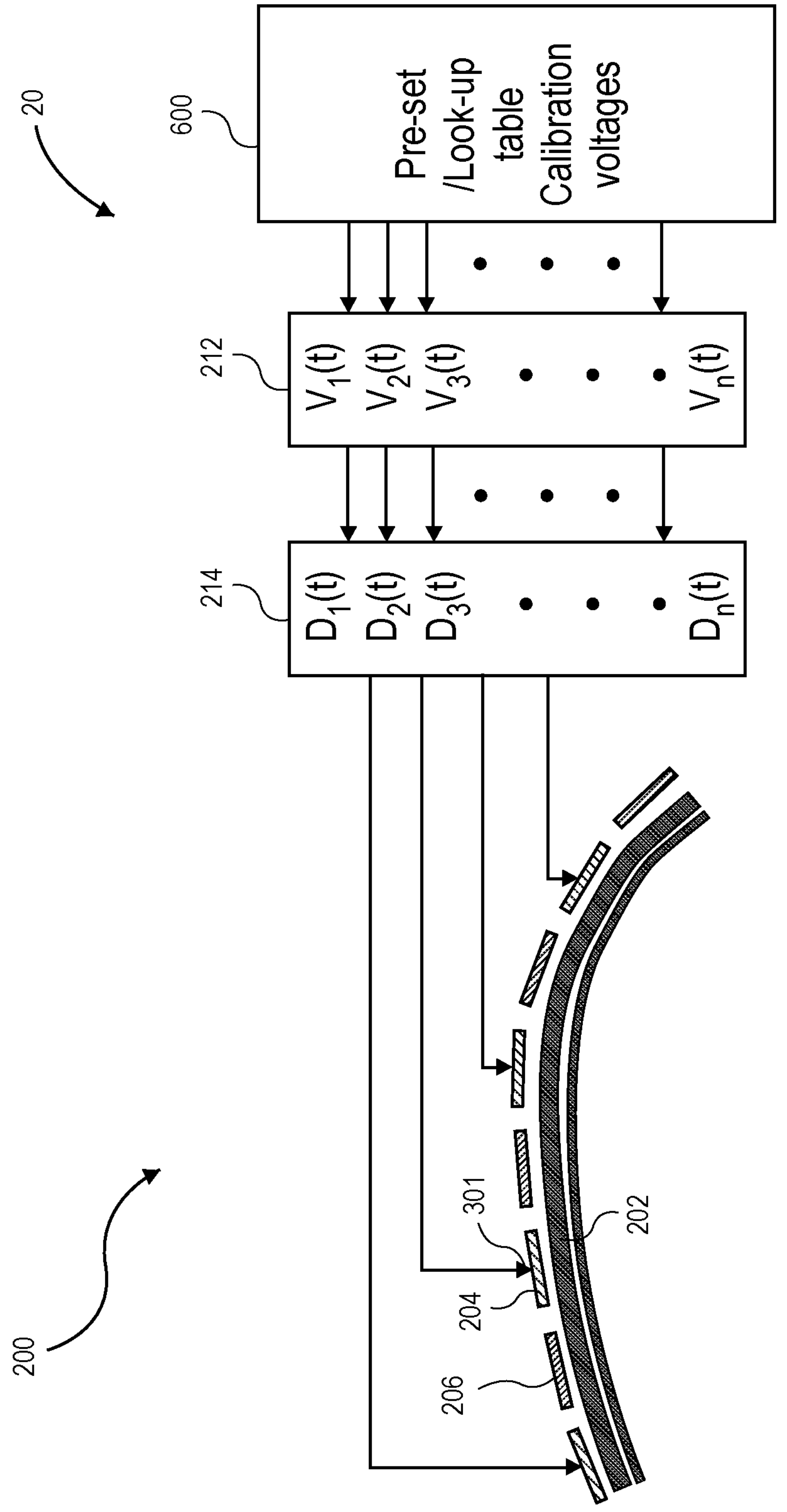
FIG. 6 illustrates another schematic view of the ultrasound sensor system, according to an example.

FIG. 6 illustrates another schematic view of the transducer array 200, according to an example. The view of FIG. 6 may be similar to that of FIG. 4, except that the application of electrical power is generally reversed; that is, the strain sensors 204 may be used as actuators. As discussed above, the piezo-polymeric material of the strain sensors 204 may generate a current based on its thickness. Conversely, application of current may cause the piezo-polymeric material to thin/thicken, and thereby cause the main body 300 (FIG. 3) of the strain sensor 204 to deform (bend). In some examples, once moved into a bent configuration, the strain sensor 204 may tend to stay in that configuration, unless/until bent to a new configuration. This may permit the ultrasound sensor system 10 to be calibrated. For example, a desired starting geometry for the flexible substrate 202 may be determined, e.g., by reference to the relative positions of the ultrasonic transducer elements 206, which may act as points on the substrate 202, and appropriate charges provided to the sensors 204 so as to form the flexible substrate 202 to this geometry.

As an example, as shown, a pre-set look-up 600 table of calibration voltages may be provided, which may correspond to the desired starting geometry, as indicated in box 212. These voltages may be provided as an array, corresponding to the individual sensors 204, as indicated in the box 600, corresponding to displacements in box 214, which may cause the flexible substrate 202 to take a desired shape and place the ultrasound transducer elements 206 in a desired starting location, e.g., reference location/plane, from which the displacement can be measured. Via an amplifier and/or other circuitry, these voltages may be applied to the individual sensors 204, which deflect to the desired, initial geometry, thereby "calibrating" the system 10.

Figure 7:
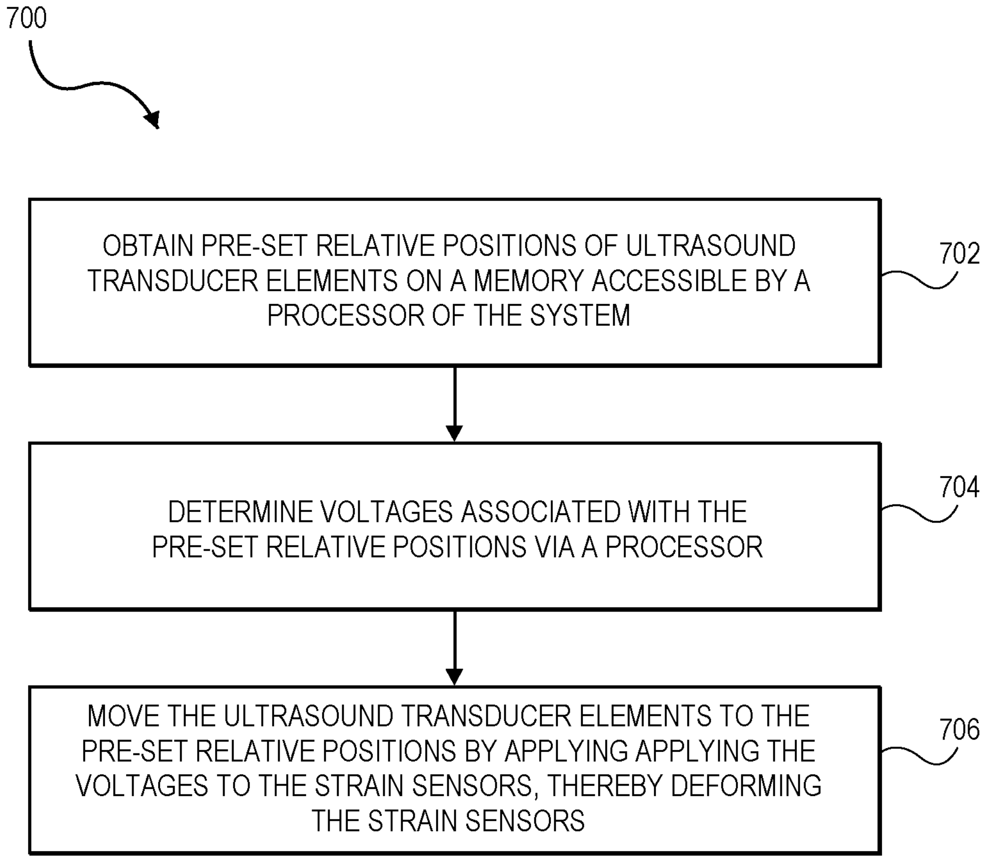
FIG. 7 illustrates a flowchart of a method for calibrating an ultrasound sensor system, according to an example.

FIG. 7 illustrates a flowchart of a method 700 for calibrating the transducer array 200 (e.g., as part of the ultrasound system 10), according to an example. The method 700 may proceed by operation of the ultrasound sensor system 10, but certain implementations may use other devices. Moreover, the method 700 may proceed by executing the steps in the order presented below, or in any other order, without departing from the scope of the present disclosure. In some examples, the steps presented herein may be combined, conducted in parallel, and/or individual steps may be partitioned into two or more steps, without departing from the scope of the present disclosure. Further, the method 700 may be employed in conjunction with and/or as part of (e.g., before, during, or after) the method 500, and thus the two methods 500, 700 should not be considered mutually exclusive.

The method 700 may begin prior to the application of the system 10 to the patient, e.g., before, during, or after integrating the system 10 at least partially into clothing to be worn by the patient, and prior to putting the clothing on. The method 700 may include loading pre-set relative positions of the ultrasound transducer elements 206 onto a memory accessible by a processor of the system 10, as at 702. Further, voltages associated with the pre-set relative positions may be loaded or determined, e.g., via a processor, as at 704. The voltages may be calculated to deform the strain sensors 204 such that they deflect to a predetermined configuration.

The method 700 may then include actuating the transducer array 200 by applying the voltages to the strain sensors 204, thereby deforming the strain sensors 204, as at 706. This may result in the ultrasound transducer elements 206 moving to a baseline configuration from which relative displacements may be determined by measuring of voltages generated by the strain sensors 204, as discussed above.

Figure 8A:
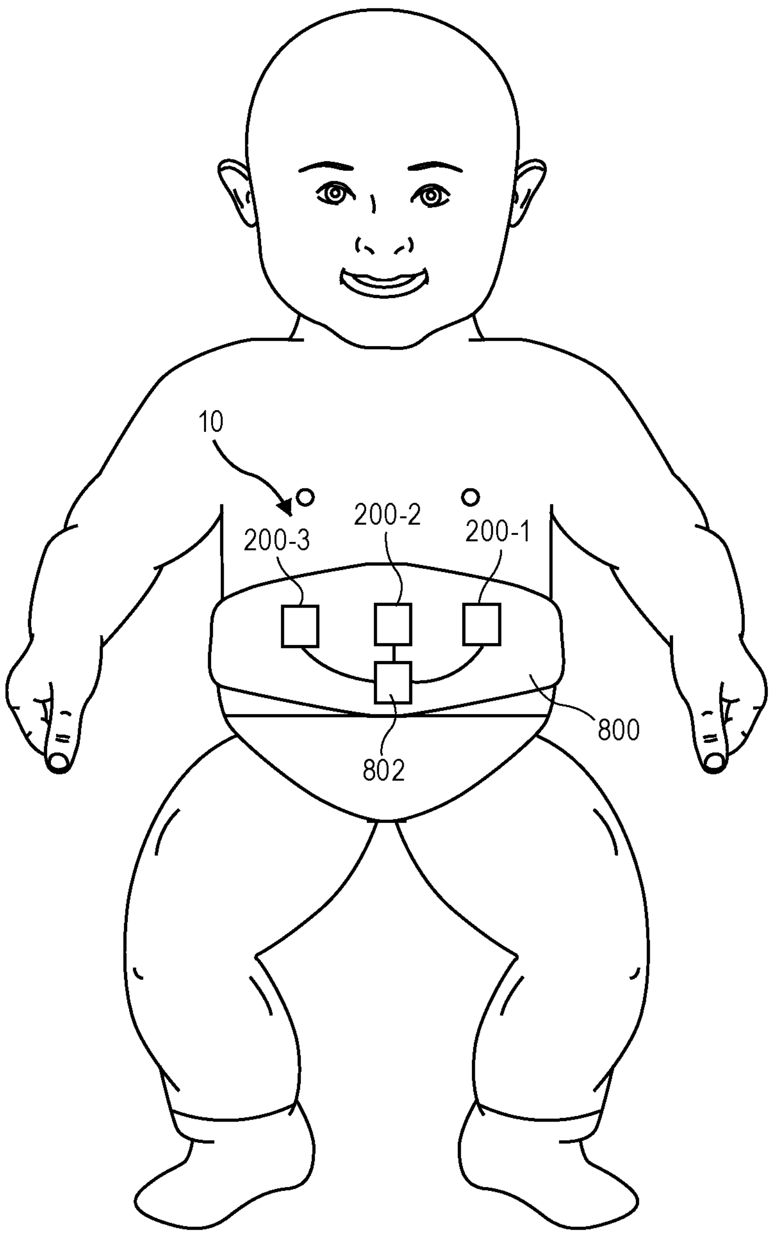
FIG. 8A illustrates an example of the ultrasound sensor system coupled to a wearable clothing garment, which may be worn by a patient such as an infant.

FIG. 8A a view of the ultrasound sensor system 10 coupled to a wearable clothing garment 800, which may be worn by a patient such as an infant. When worn, the ultrasound sensor system 10 coupled to the garment 800 may not require gel, but the transducer array 200 may be impedance-matched to the skin of the patient. Further, the flexible construction of the transducer array 200 may promote a comfortable fit, which may conform to the body of the patient as the patent moves. In at least some examples, several transducer arrays 200 (200-1, 200-2, 200-3) may be provided, and may be connected together and/or to a processor 802 via conductive cables 804. The processor 802 may be disposed on an outside surface of the garment. The transducer arrays 200-1, 200-2, 200-3 may be disposed on an inner surface of the garment 800 and oriented so that the transducer elements 206 (FIG. 2) face the infant's body (e.g., heart, lungs, gastrointestinal organs, etc.). The wearable clothing garment 800 may be designed to be comfortable on the patient. For example, the wearable clothing garment 800 may be made of cotton or another lightweight, potentially stretchable material that is thin, soft, breathable, and cool. An external display may be connected to the processor 802 in order to provide a visualization of images generated based on signals emitted/acquired by the transducer array(s) 200. In some examples, the garment 800 may be a belt, as shown, but in others could be any type of garment wearable by an infant.

Figure 8B:
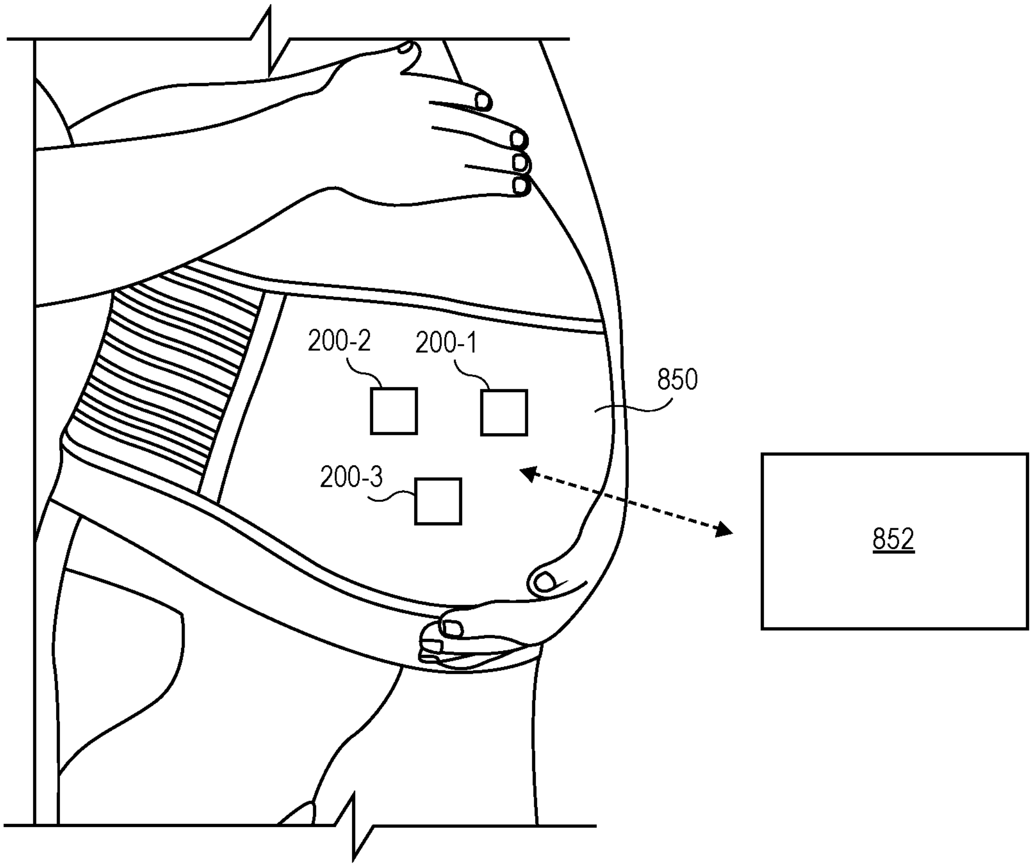
FIG. 8B illustrates another view of the ultrasound sensor system coupled to a wearable clothing garment, e.g., a belt worn by a patient such as a pregnant mother.

As noted above, in some examples, the transducer array 200 may be used to measure heartrate, respiratory rate, etc., of a mother, as well as or, instead, a heartrate of a fetus within the mother. FIG. 8B illustrates an abdomen of a pregnant mother with a wearable garment, such as a band or belt 850 attached thereto. The belt 850 may include one or more transducer arrays (200-1, 200-2, 200-3), such as the transducer array 200, therein. The transducer arrays 200-1, 200-2, 200-3 may be disposed on an inner surface of the belt 850 and oriented so that the transducer elements 206 (FIG. 2) face the abdomen. The flexible belt 850 may be designed to be comfortable on the patient. For example, the flexible belt 850 may be made of a stretchable mesh material (e.g., similar to the material utilized with postpartum underwear), that is thin, soft, breathable, and cool. The flexible belt 850 may also be stretchy so as to conform to the different sizes of patients. In certain implementations, the flexible belt 850 may have full openings on respective ends (e.g., superior and inferior ends) to enable the flexible belt 850 to be slid along the patient's body until is disposed about the abdomen. In certain implementations, the flexible belt 8500 may be adjustable for fit and wrapped around the abdomen of the patient (e.g., similar to abdominal binders) and secured via fasteners (e.g., hook and loop fasteners).

The transducer array 200 may be flexible and able to automatically compensate for displacement of its individual transducer elements 206 in its signal processing routines. Accordingly, the transducer array 200 may not impair the flexibility of the belt 850, but may flex with it, while still maintaining accurate signal processing. The transducer array(s) 200 may be in communication with a monitor 852, via wired or wireless connection. The monitor 1002 may receive data from the transducer array(s) 200 and convert the data to images, metrics (e.g., heartrate, uterine activity), etc. Further, the monitor 852 (and/or one or more processing components that are on-board the transducer arrays 200 and/or the belt 850) may provide steering commands for the transducer array 200.

Further, the transducer elements 206 may be steerable. For example, when a fetus in the uterus moves, the focus of the transducer elements 206 may be adjusted via one or more algorithms to change the focus of the transducer elements 206. For example, the timing (e.g., of the firing or triggering) of the transducer elements 206 may be adjusted. A processer may determine that a signal is not being acquired (e.g., low signal strength) and/or is otherwise out of focus. In response, the processor may signal to the transducer array 200 to begin a scanning sequence, in which the transducer array 200 may search for a signal across a variety of locations. Once a location is known, a beamforming algorithm may be tuned to focus on different regions. For example, a beamforming algorithm adjusts the time-delay parameters for transmission and reception to focus at a particular location. Fetal localization data may be used to guide changes to the focal laws (i.e., mathematical formulas utilized for firing) to focus the beams. This enables the fetal heart rates of all of the fetuses to be simultaneously and continuously monitored even when the fetuses move. In addition, this avoids having to reposition the single transducer (and belt) to accommodate for movement of the fetuses.

Figure 9:
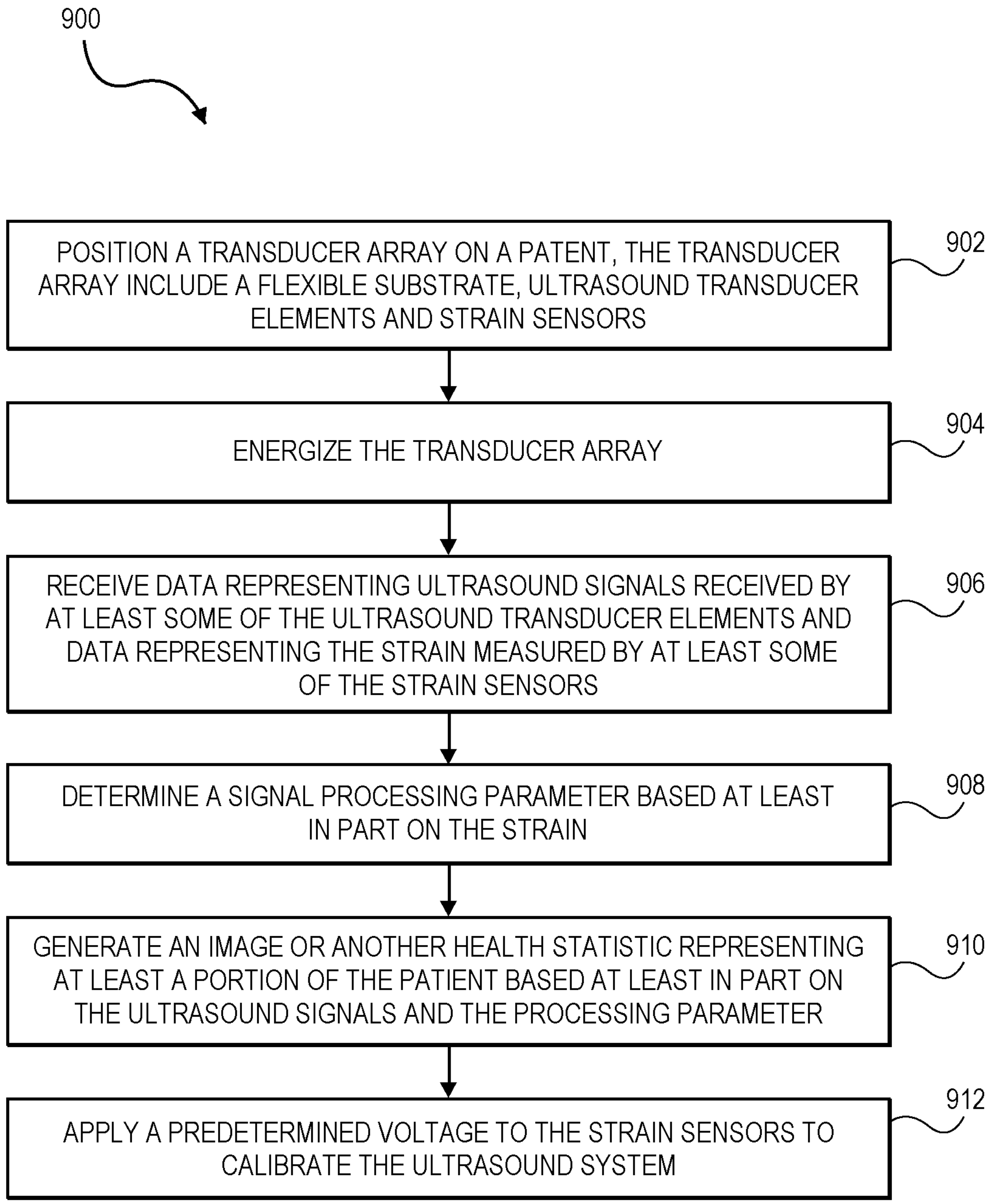
FIG. 9 illustrates a flowchart of a method for operating an ultrasound sensor system, according to an example.

FIG. 9 illustrates a flowchart of a method 900 for operating an ultrasound sensor system 10, according to an example. The method 900 may proceed by operation of the ultrasound sensor system 10, but certain implementations may use other devices. Moreover, the method 900 may proceed by executing the steps in the order presented below, or in any other order, without departing from the scope of the present disclosure. In some examples, the steps presented herein may be combined, conducted in parallel, and/or individual steps may be partitioned into two or more steps, without departing from the scope of the present disclosure. Further, the method 900 may be employed in conjunction with and/or as part of (e.g., before, during, or after) any of the methods 500 and/or 700 or others presented herein, and thus the methods presented herein should not be considered mutually exclusive.

The method 900 may include positioning a transducer array 200 on a patent, as at 902. In at least some examples, the transducer array 200 may be coupled to (e.g., sewn, adhered, embedded, or otherwise connected to and, in some cases, forming part of) a clothing garment. Thus, the positioning at 902 may include putting the clothing garment on the patent. The patient may be an infant or a pregnant mother). The transducer array 200 includes a flexible substrate 202, a plurality of ultrasound transducer elements 206 disposed on the flexible substrate 202, and a plurality of strain sensors 204 coupled to the flexible substrate 202 and configured to generate signals representing a strain in the flexible substrate 202 generated by flexing the flexible substrate. The method 900 may also include energizing the transducer array 200, as at 904, such that at least some of the plurality of ultrasound transducer elements 206 emit and receive ultrasound signals and the strain sensors 204 measure the strain in the flexible substrate 202. The transducer array 200 may be energized by, e.g., directing electrical current from a power source, such as a battery, to the individual transducer elements 206 and/or other circuitry of the transducer array 200, such that the transducer elements 206 are operable to emit and receive ultrasound signals.

The method 900 may further include receiving, using a processor (e.g., part of the ASIC 20 of FIG. 1), data representing the ultrasound signals received by at least some of the ultrasound transducer elements 206 and data representing the strain measured by at least some of the strain sensors 204, as at 906. The method 900 may then include determining, using the processor, a signal processing parameter based at least in part on the strain, as at 908. For example, the signal processing parameter may be a beamforming parameter such as a time-delay parameter, which may be used by the process to adjust the signals received by the transducer elements 206 to account for the different positions of the transducer elements 206, e.g., different distances from the constant phase front 402 (FIG. 4). This calculation may be achieved by using the strain measurement to infer a displacement of the individual ultrasound transducer elements 206 (e.g., relative to one another or to a reference position/plane), from which the position of the ultrasound transducer elements 206, relative to one another, can be determined. The signal processing (e.g., time-delay) parameter may be inversely related to the distance of the transducer elements 206 from the constant phase front 402. Accordingly, the signal processing parameter may be determined at least partially based on the measurements acquired by the strain sensors 204.

In at least some examples, the strain sensors 204 may be configured to measure a stretch and a stretch direction. Accordingly, not only the displacement distance but the direction of the displacement may be calculated, in some examples, which may permit an accurate measurement of the localized geometry of the flexible substrate 202 and thus the relative positioning of the ultrasound transducer elements 206. As such, the signal processing parameter may be calculated at least partially based on the stretch and stretch direction.

The method 900 may then include generating an image (e.g., generating an image of data) or another health statistic representing at least a portion of the patient based at least in part on the ultrasound signals and the processing parameter, as at 910.

For example, the image may represent a heartrate of a fetus, infant, or mother. In another example, the image may represent a visual depiction of internal organs or other tissues of the patient, e.g., brain, heart, gastrointestinal system, lungs, etc. In various examples, the image represents one or more of lungs, body fluid status, cardiac status, heart rate, respiration rate, gastrointestinal status, brain development. Based on this data (e.g., heartrate and/or images), a health (or aspect thereof) of the patient may be inferred.

Further, in at least some examples, the images may be received continuously and may be employed to assist with positioning of tools or other implements during surgical operations, e.g., "guiding" medical procedures on the patent using the images to provide real-time, visual feedback to a surgeon. Examples of such procedures may include inserting a tube into the patient (e.g., a chest tube, breathing tube, arterial line, etc.). Further, such imaging may also be conducted continuously, for a duration of time, e.g., after inserting such a tube, to ensure the tube remains properly in place. This may be done, in some examples, instead of relying on periodic X-rays that may harm the patient.

In other examples, such continuous ultrasonic imaging may be employed during pregnancy for eliminating fetal heartrate (FHR) and maternal heartrate (MHR) confusion, multifetal FHR monitoring, true labor detection using cervical images (dilation measurement), home monitoring until true labor, when to go to hospital alert, contraction monitoring, and/or home monitoring for high-risk patients. Further, applications may include, during labor and delivery, FHR/MHR confusion elimination, fetal descent measurement, fetal position measurement at any stage of labor, labor progression (e.g., cervical images for non-invasive dilation measurement), lower pelvis/fetal head images for effective pushing in second stage, avoiding repositioning with labor progression, fetal movement detection, multifetal FHR, multifetal FMD, and/or contraction monitoring. The applications may also include post-partum hemorrhage detection and/or imaging post-partum for other conditions.

In some examples, the method 900 may also include a process for calibrating the transducer array 200. For example, the method 900 may include applying a predetermined voltage to the strain sensors, as at 912. As noted above, the strain sensor 904 may act as actuators when a voltage is applied thereto, e.g., flexing in response thereto. Accordingly, in addition to responding to a strain applied thereto, the strain sensors 904 may apply a strain in response to the application of a voltage. Thus, a predetermined starting geometry for the flexible substrate 202 may be imposed by application of voltage to the strain sensors 204. As a result, an initial or "reference" position for the individual ultrasound transducer elements 206 may be enforced, so as to calibrate a position of the ultrasound transducer elements 206 relative to one another.

Technical effects of the disclosed subject matter include providing a wearable, flexible ultrasound sensor system that may be configured for continuous monitoring of a patient. The ultrasound sensor system may be "steerable" such that it is able to change its focus to accommodate movement of the target (e.g., a fetus within a mother). The ultrasound sensor system may also be tailored for use on a small, fragile patient such as an infant. The ultrasound sensor system may be able to be employed without gel, as its transducers may be impedance-matched.

Further, the ultrasound sensor system may automatically adjust based on its changing geometry. That is, stretchable strain sensors may be included on a flexible substrate upon which ultrasonic transducer elements are positioned. The flexible substrate accommodates the transducer array flexing with the movement of the patient, while the strain sensors permit measuring instantaneous displacement of the ultrasound transducer elements relative to one another, and thereby account for the changing location of the ultrasound transducer elements brought on by movement of the patent. Accordingly, signals acquired by the individual transducer elements may be aligned/targeted, such that coherent images may be produced, despite the difference in distances between the individual transducer elements and a constant phase front relative to the focal point (target) of the transducer elements. Further, the present invention may be calibrated by applying voltages applied to the strain sensors to place the ultrasound transducers in a predetermined position, thereby permitting an accurate and repeatable tracking of the relative positions of the ultrasound transducer elements.

Figure 10:
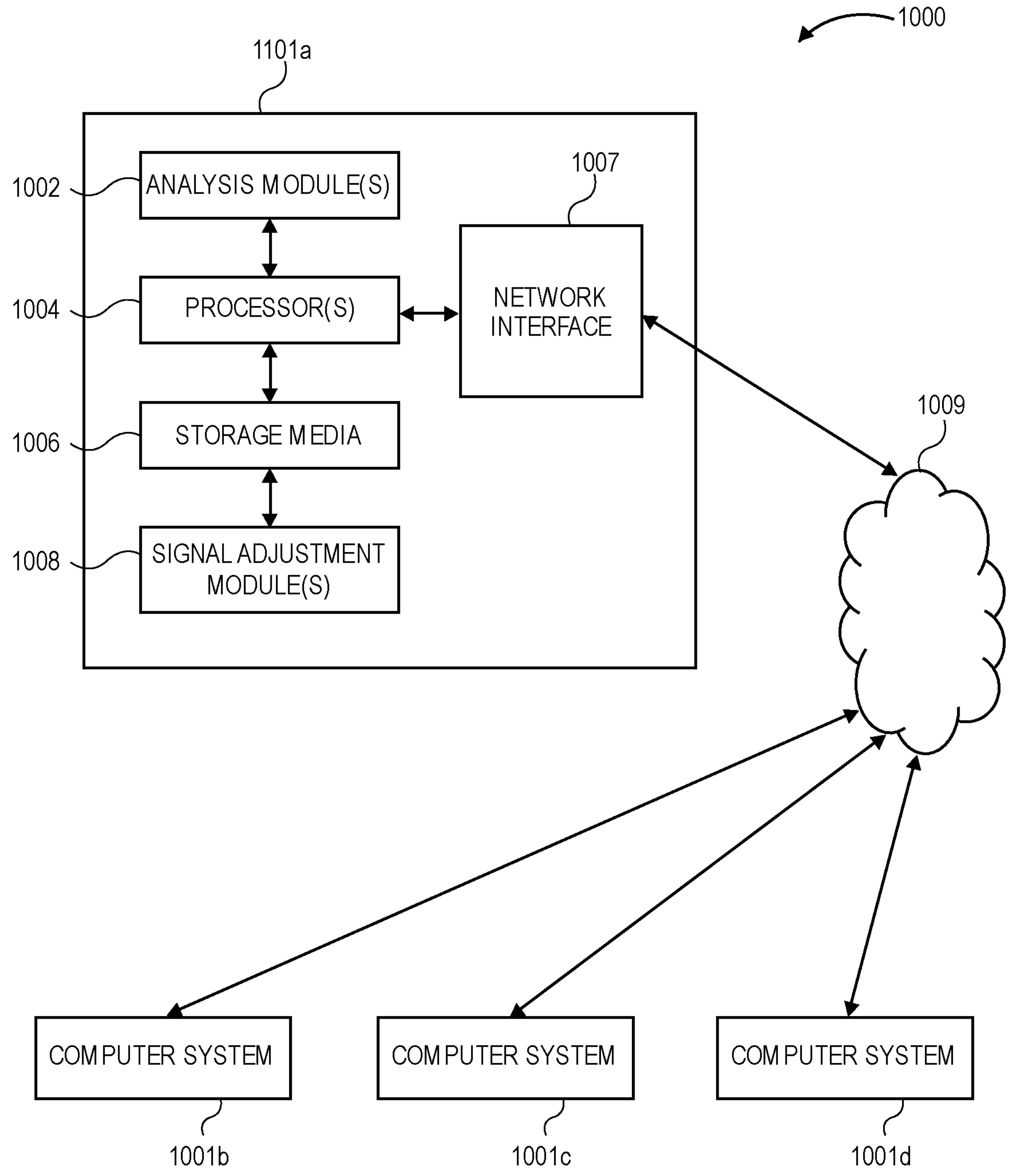
FIG. 10 illustrates a schematic view of a computing system, according to an implementation.

In some examples, any of the methods of the present disclosure may be executed by a computing system. For example, as described above, the transducer array 200 may include or be connected to one or more ASICs 20 (FIG. 1), which may each be represented as a computing system. Further, various monitoring, signal processing, steering, and/or other processors may be provided and linked together to provide a desired functionality, as described above. FIG. 10 illustrates an example of such a computing system 1000, in accordance with some examples. The computing system 1000 may include a computer or computer system 1001A, which may be an individual computer system 1001A or an arrangement of distributed computer systems (each including one or more processors). The computer system 1001A includes one or more analysis module(s) 1002 configured to perform various tasks according to some examples, such as one or more methods disclosed herein. To perform these various tasks, the analysis module 1002 executes independently, or in coordination with, one or more processors 1004, which is (or are) connected to one or more storage media 1006. The processor(s) 1004 is (or are) also connected to a network interface 1007 to allow the computer system 1001A to communicate over a data network 1009 with one or more additional computer systems and/or computing systems, such as 1001B, 1001C, and/or 1001D (note that computer systems 1001B, 1001C and/or 1001D may or may not share the same architecture as computer system 1001A, and may be located in different physical locations, e.g., computer systems 1001A and 1001B may be located in a processing facility, while in communication with one or more computer systems such as 1001C and/or 1001D that are located in one or more data centers, and/or located in varying countries on different continents).

A processor can include a microprocessor, microcontroller, processor module or subsystem, programmable integrated circuit, programmable gate array, or another control or computing device.

The storage media 1006 can be implemented as one or more computer-readable or machine-readable storage media. Note that while in the example of FIG. 10 storage media 1006 is depicted as within computer system 1001A, in some examples, storage media 1006 may be distributed within and/or across multiple internal and/or external enclosures of computing system 1001A and/or additional computing systems. Storage media 1006 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLURAY® disks, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some examples, computing system 1000 contains one or more signal adjustment module(s) 1008. In the example of computing system 1000, computer system 1001A includes the signal adjustment module 1008. In some examples, a single signal adjustment module may be used to perform some or all aspects of one or more examples of the methods. In alternate examples, a plurality of signal adjustment modules may be used to perform some or all aspects of methods.

It should be appreciated that computing system 1000 is only one example of a computing system, and that computing system 1000 may have more or fewer components than shown, may combine additional components not depicted in the example of FIG. 10, and/or computing system 1000 may have a different configuration or arrangement of the components depicted in FIG. 10. The various components shown in FIG. 10 may be implemented in hardware, software, or a combination of both hardware and software, including one or more signal processing and/or application specific integrated circuits.

Further, the steps in the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of protection of the invention.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. § 112(f). However, for any claims containing elements designated in any other manner, it is intended that such elements are not to be interpreted under 35 U.S.C. § 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound system, comprising:

a transducer array, comprising:

a flexible substrate;

ultrasound transducer elements disposed on the flexible substrate and configured to transmit and acquire ultrasound signals that propagate in a body of a patient, and wherein the ultrasound transducer elements are configured to flex with the flexible substrate; and strain sensors coupled to or integrated into the flexible substrate and configured to measure a strain in the flexible substrate generated by flexing the flexible substrate; and wherein the transducer array is coupled to a wearable band configured to be secured to an abdomen of a patient, wherein the patient is a pregnant mother, and wherein the transducer array is configured to detect a heart rate of one or more fetuses in the pregnant mother, a heart rate of the mother, uterine activity within the pregnant mother, fetal movement, fetal position and descent, or a combination thereof; and a processor coupled to the ultrasound transducer elements and the strain sensors, wherein the processor is configured to process the signals acquired by the ultrasound transducer elements based at least in part on the strain measured by the strain sensors, and wherein the processor is configured to calculate positions of the ultrasound transducer elements relative to one another based at least in part on the strain, and wherein the processor is configured to continuously modify transmission and reception time-delay parameters based at least in part on the calculated positions, and wherein the processor uses the time-delay parameters to adjust signals received by the ultrasound transducer elements to account for different positions of the ultrasound transducer elements.

2. The ultrasound system of claim 1, wherein the strain sensors are configured to measure a stretch, a stretch direction, or both, and wherein the processor is configured to calculate the positions of the ultrasound transducer elements relative to one another based at least in part on the stretch, the stretch direction, or a combination thereof.

3. The ultrasound system of claim 2, wherein the processor is configured to construct an image based on the ultrasound signals, and wherein the image represents one or more of lungs, body fluid, cardiac imaging, hear rate, respiration rate, gastrointestinal organs, or brain development.

4. The ultrasound system of claim 1, wherein the strain sensors are disposed on the flexible substrate.

5. The ultrasound system of claim 1, wherein the strain sensors are interspersed with the ultrasound transducer elements on the flexible substrate.

6. The ultrasound system of claim 1, wherein the transducer array is configured to be coupled to a clothing garment that is worn by the patient, and wherein the patient is an infant.

7. The ultrasound system of claim 1, wherein the transducer array is configured to continuously transmit signals to the processor, and wherein the processor is configured to continuously interpret the signals to monitor a health of the patient.

* * * * *